United States Patent [19]

Avidan et al.

[11] Patent Number: 4,873,389
[45] Date of Patent: Oct. 10, 1989

[54] CONVERSION OF LIGHT OLEFINS TO GASOLINE USING LOW-TEMPERATURE CATALYST REGENERATION

[75] Inventors: Amos A. Avidan, Yardley; David L. Johnson, Glen Mills, both of Pa.

[73] Assignee: Mobil Oil Corp., New York, N.Y.

[21] Appl. No.: 228,147

[22] Filed: Aug. 4, 1988

[51] Int. Cl.⁴ .............................................. C07C 2/02
[52] U.S. Cl. .................................. 585/533; 585/415; 585/733
[58] Field of Search ................ 585/533, 415, 733; 502/41

[56] References Cited

U.S. PATENT DOCUMENTS

| | | | |
|---|---|---|---|
| 3,760,024 | 9/1973 | Cattanach | 260/673 |
| 3,845,150 | 10/1974 | Yan et al. | 260/673.5 |
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,333,185 | 2/1984 | Tabak | 585/312 |
| 4,456,779 | 6/1984 | Owen et al. | 585/415 |
| 4,497,968 | 2/1985 | Wright et al. | 585/304 |
| 4,746,762 | 5/1988 | Avidan et al. | 585/415 |

*Primary Examiner*—Curtis R. Davis
*Attorney, Agent, or Firm*—Alexander J. McKillop; Charles J. Speciale; Robert B. Furr, Jr.

[57] ABSTRACT

A fluidized bed catalytic process is disclosed for the conversion of light olefinic gas feedstock to produce hydrocarbons rich in $C_5+$ liquids. Low temperature turbulent fluidized bed regeneration preserves the acid activity of the catalyst thus reducing catalyst makeup requirements.

17 Claims, 2 Drawing Sheets

CONVERSION OF LIGHT OLEFINS TO GASOLINE USING LOW-TEMPERATURE CATALYST REGENERATION

BACKGROUND OF THE INVENTION

This invention relates to a catalytic technique for upgrading a light aliphatic feedstream to heavier hydrocarbons. In particular, it provides a continuous process for oligomerizing a light olefinic gas feedstock, containing ethene, propene or other lower alkenes, to produce $C_4+$ hydrocarbons, such as olefinic liquid fuels, isobutane, aromatics and other useful products. Ethene (ethylene, $C_2H_4$) -containing gases, such as petroleum cracking offgas, are particularly useful feedstocks herein. A novel catalyst regeneration technique is used to dramatically reduce catalyst makeup rate.

Developments in zeolite catalysis and hydrocarbon conversion processes have created interest in utilizing olefinic feedstocks for producing $C_5+$ gasoline, diesel fuel, etc. In addition to basic chemical reactions promoted by medium-pore zeolite catalysts, a number of discoveries have contributed to the development of new industrial processes. These are safe, environmentally acceptable processes for utilizing feedstocks that contain lower olefins, especially $C_2$–$C_4$ alkenes. Conversion of $C_2$–$C_4$ alkenes and alkanes to produce aromatics-rich liquid hydrocarbon products were found by Cattanach (U.S. Pat. No. 3,760,024) and Yan et al. (U.S. Pat. No. 3,845,150) to be effective processes using ZSM-5 zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062; 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Product distribution for liquid hydrocarbons can be varied by controlling process conditions, such as temperature, pressure and space velocity. Gasoline ($C_5$–$C_{10}$) is readily formed at elevated temperatrue (e.g. up to about 400° C.) and moderate pressure from ambient to about 5500 kPa, preferably about 250 to 2900 kPa. Olefinic gasoline can be produced in good yield and may be recovered as a product or fed to a low severity, high pressure reactor system for further conversion to heavier distillate-range products. Distillate mode operation can be employed to maximize production of $C_{10}+$ aliphatics by reacting the lower and intermediate olefins at high pressure and moderate temperature. Operating details for typical "MOGD" oligomerization units are disclosed in U.S. Pat. Nos. 4,456,779; 4,497,968 (Owen et al.) and 4,433,185 (Tabak), incorporated herein by refernce. At moderate temperature and relatively high pressure, the conversion conditions favor distillate-range product having a normal boiling point of at least 165° C. (330° F.). Lower olefinic feedstocks containing $C_2$–$C_6$ alkenes may be converted selectively; however, the low severity distillate mode conditions do not convert a major fraction of ethene. While propene, butene-1, and others may be converted to the extent of 50% to 95% in the lower severity moderate temperature distillate mode, only about 10% to 30% of the ethene component will be converted using HZSM-5 or similar acid zeolites. Many feedstocks of commercial interest, such as FCC offgas, dehydrogenation products, ethane cracking by-product, etc., contain both ethene and hydrogen along with $H_2S$ and light aliphatics. Ethene can also be converted at moderate temperature with a bifunctional nickel catalyst.

U.S. Pat. No. 4,746,762 to Avidan et al., incorpoated by reference as if set forth at length herein, teaches a process for upgrading an ethene-rich olefinic light gas to a liquid hydrocarbon rich in olefinic gasoline, isobutane and aromatics by catalytic conversion in a turbulent fluidized bed of solid acid zeolite catalyst under high serevity reaction conditions in a single pass or with recycle of gas product. The process is particularly useful for upgrading FCC light gas, which usually contains significant amounts of ethene, propene, $C_2$–$C_4$ paraffins and hydrogen produced in cracking heavy petroleum oils or the like. During such an upgrading process, the catalyst accumulates coke and is progressively deactivated. The deactivated catalyst is then regenerated by burning off the coke as the catalyst is fluidized in a stream of oxygen-containing inert gas at elevated temperatures typically ranging from 480° C. to 705° C.

Water is evolved from the combustion of coke during regeneration creating steam in the regenerator vessle. The medium-pore zeolite catalysts permanently deactivate upon contact with water at elevated temperatures at a rate believed to be proportional to an integral function of temperature and partial pressure of water. This phenomenon is commonly referred to as "steaming deactivation". Surprisingly, it has been found that coked catalyst from an olefin upgrading process such as described above can be regenerated at temperatures lower than previously believed possible. Further, such low temperature regeneration dramatically reduces steaming deactivation and extends the useful like of the catalyst. Fresh make-up catalyst represents a substantial portion of the total operating costs for a catalytic aromatization process. Consequently, longer catalyst life yields a significant savings in operating costs.

SUMMARY OF THE INVENTION

An improved process has been found for continuous conversion of an aliphatic feedstock to heavier hydrocarbon products wherein the feedstock is contacted at elevated temperature with a fluidized bed of zeolite catalyst under conversion conditions and regeneration conditions are selected to maximize the active life of the catalyst. The process of the present invention comprises the steps of fluidizing a catalyst in a reactor zone by passing feedstock upwardly through the reaction zone under conversion conditions at a velocity greater than the dense bed transition velocity in a turbulent regime and less than transport velocity for the average catalyst particle; withdrawing a portion of coked catalyst from the reaction zone; oxidatively regenerating the withdrawn catalyst in a turbulent regenerator bed at a temperature between 400° C. and 480° C. and returning regenerated catalyst to the reaction zone. The process may further comprise returning regenerated catalyst to the reaction zone at a rate to control catalyst activity and reaction severity such that the $C_3$–$C_5$ alkane:alkene ratio in the hydrocarbon product is maintained at about 0.1:1 to 200:1 and preferably less than 50:1.

DETAILED DESCRIPTION

Aromatization Process

Figure 1:
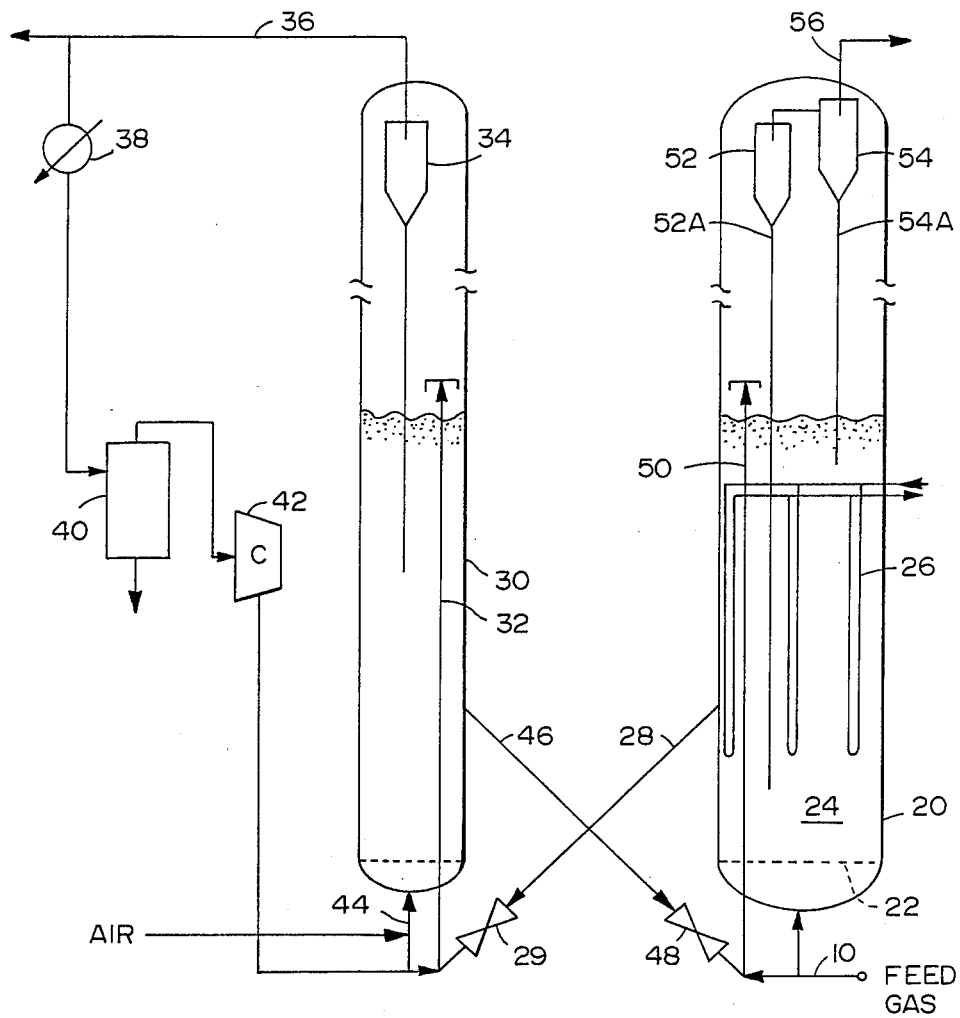
FIG. 1 is a simplified schematic view of a fluidized bed reactor system according to the present invention.

In this description, metric units and parts by weight are employed unless otherwise stated.

The preferred feedstock contains $C_2$-$C_6$ alkenes (mono-olefin) including at least 2 mole % ethene, wherein the total $C_2$-$C_3$ alkenes are in the range of about 10 to 40 wt %. Non-deleterious components, such as methane and other paraffins and inert gases, may be present. Some of the paraffins in the feed will also convert to $C_4+$ hydrocarbons, depending on reaction conditions and the catalyst employed. A particularly useful feedstock is a light gas by-product of FCC gas oil cracking units containing typically 10-40 mol % $C_2$-$C_4$ olefins and 5-35 mol % $H_2$ with varying amounts of $C_1$-$C_3$ paraffins and inert gas, such as $N_2$. The process may be tolerant of a wide range of lower alkanes, from 0 to 95%. Preferred feedstocks contain more than 50 wt. % $C_1$-$C_4$ lower aliphatic hydrocarbons, and contain sufficient olefins to provide total olefinic partial pressure of at least 50 kPa. Under the high severity reaction conditions employed in the present invention, lower alkanes may be partially converted to $C_4+$ products, especially propane.

The desired products are $C_4$ to $C_9$ hydrocarbons, which will comprise at least 50 wt. % of the recovered product, preferably 80% or more. While olefins may be a predominant fraction of the $C_4+$ reaction effluent, up to 45% butenes, pentenes, hexenes, heptenes, octenes, nonenes and their isomers; it is desired to upgrade the feedstock to high octane gasoline containing aromatics, preferably at least 10% by weight.

The reaction severity conditions can be controlled to optimize yield of $C_4$-$C_9$ aliphatic hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh catalyst having acid activity or by controlling catalyst deactivation and regeneration rates to provide an apparent average alpha value of about 1 to 80.

Reaction temperatures and contact time are also significant factors in the reaction severity, and the process parameters are followed to give a substantially steady state condition wherein the reaction severity index (R.I.) is maintained within the limits which yield a desired weight ratio of propane to propene. While this index may vary from about 0.1 to 200, it is preferred to operate the steady state fluidized bed unit to hold the R.I. at about 0.2:1 to 5:1 in the absence of added propane. While reaction severity is advantageously determined by the weight ratio of propane:propene in the gaseous phase, it may also be approximated by the analogous ratios of butanes:butenes, pentanes:pentenes, or the average of total reactor effluent alkanes:alkenes in the $C_3$-$C_5$ range. Accordingly, these alternative expressions may be a more accurate measure of reaction severity conditions when propane is added to the feedstock. The optimum value will depend upon the exact catalyst composition, feedstock and reaction conditions; however, the typical ethene-rich light gas mixtures used in the examples herein and similar cracking process off-gas can be optionally upgraded to the desired aliphatic-rich gasoline by keeping the R.I. at about 1.

Upgrading of olefins by such hydrogen contributors in fluidized bed cracking and oligomerization units is taught by Owen et al in U.S. Pat. No. 4,090,949. This technique is particularly useful for operation with a fluidized catalytic cracking (FCC) unit to increase overall production of liquid product in fuel gas limited petroleum refineries. Light olefins and some of the light paraffins, such as those in FCC fuel gas, can be converted to valuable $C_4+$ hydrocarbon product in a fluid-bed reactor containing a zeolite catalyst. In addition to fuel gas upgrading, the load to the refinery fuel gas plant is decreased considerably. This allows operation of the FCC unit at higher throughput and/or higher severity in fuel gas limited refineries.

The use of fluidized bed catalysis permits the conversion system to be operated at low pressure drop, which in an economically practical operation can provide a maximum operating pressure only 50 to 200 kPa above atmospheric pressure. Another important advantage is the close temperature control that is made possible by turbulent regime operation, wherein the uniformity of conversion temperature can be maintained within close tolerances. Except for a small zone adjacent the bottom gas inlet, the midpoint measurement is representative of the entire bed, due to the thorough mixing achieved.

In a typical process, the ethene-rich $C_2+$ olefinic feedstock is converted in a catalytic reactor under oligomerization conditions and moderate pressure (i.e. 100 to 2500 kPa) to produce at least 6% isobutane and a predominantly liquid product consisting essentially of $C_4+$ hydrocarbons rich in gasoline-range olefins and aromatics.

Reactor Operation

A typical reactor unit employs a temperature-controlled catalyst zone with indirect heat exchange and/or adjustable gas quench, whereby the reaction exotherm can be carefully controlled to prevent excessive temperature above the usual operating range of about 315° C. to 510° C., preferably at average reactor temperature of 315° C. to 430° C. Energy conservation in the system may utilize at least a portion of the reactor exotherm heat value by exchaning hot reactor effluent with feedstock and/or recycle streams. Optional heat exchangers may recover heat from the effluent stream prior to fractionation. Part of all of the reaction heat can be removed from the reactor without using the indirect heat exchange tubes by using cold feed, whereby reactor temperature can be controlled by adjusting feed temperature. The internal heat exchange tubes can still be used as internal baffles which lower reactor hydraulic diameter, and axial and radial mixing. The reactor typically operates at moderate pressure of about 100 to 3000 kPa, preferably 300 to 2000 kPa.

The weight hourly space velocity (WHSV, based on total olefins in the fresh feedstock) is about 0.1-5 WHSV. Typcial product fractionation systems are described in U.S. Pat. Nos. 4,456,779 and 4,504,693 (Owen et al.). Typical product distributions are set forth in U.S.

Pat. No. 4,476,762, incorporated by reference as if set forth at length herein.

Regenerator Operation

Coke accumulates on the catalyst particles during the conversion reaction. This accumulation blocks access to the catalyst pores and prevents contact between reactants and the active catalyst sites. The catalyst must then be regenerated by removing the accumulated coke. In the process of the present invention, the catalyst is regenerated at a temperature of between 400° C. and 480° C. to minimize loss of acid activity.

While not set forth to limit the invention by theory, it is believed that regenereation of the catalyst at low temperatures is possible due to the nature of the coke produced by the hydrocarbon conversion reaction of the present invention. Coke-deactivated catalyst from other fluidized bed processes, e.g. fluid catalytic cracking, requires temperatures of 480° C. to 705° C. for effective coke removal.

Under the mild severity regeneration conditions employed in the present invention, it is of particular importance to assure uniform contact between the oxygen-containing regeneration gas and the catalyst particles. Such contact may most readily be achieved by fluidizing the deactivated catalyst in a stream of oxygen-containing inert gas at a superficial velocity sufficient to maintain the fluidized mixture in a turbulent sub-transport flow regime.

Preferably, the turbulent bed has a superficial vapor velocity of about 0.3 to 2 meters per second (m/sec). At higher velocities entrainment of fine particles may become excessive and beyond about 3 m/sec the entire bed may be transported out of the regeneration zone. At lower velocities, the formation of large bubbles or gas voids can interfere with uniform contact between the regeneration gas and the catalyst particles, which contact is essential to the combustion of coke deposits.

A convenient measure of turbulent fluidization is the bed density. A typical turbulent bed has an opening density of about 100 to 500 kg/m$^3$, preferably about 300 to 500 kg/m$^3$, measured at the bottom of the regeneration zone, becoming less dense toward the top of the regeneration zone, due to pressure drop and particle size differentiation. This density is generally between the catalyst concentration employed in dense beds and the dispersed transport systems. Pressure differential between two vertically spaced points in the regenerator can be measured to obtain the average bed density at the selected section of the regenerator.

It has also been found that when regeneration severity is reduced, maintenance of a turbulent sub-transport flow regime becomes increasingly important for coke removal. Lower regenerator temperatures must be accompanied by uniform contact between the coked catalyst particles and the regeneration gas. While not introduced to limit the invention by theory, it is believed that uniform contact between regeneration gas and coked catalyst minimizes mass transfer limitations on the combustion reaction rate. On the other hand, low superficial gas velocities, e.g. below 0.1 m/sec, cause formation of large bubbles which effectively allow a portion of the regeneration gas to flow through the catalyst bed without contacting coked catalyst.

Catalysts

Developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or cystalline metal-losilicate having one or more tetrahedral species having varying degrees of acidity. ZSM-5 crystalline structure is readily recognized by its X-ray diffraction pattern, which is described in U.S. Pat. No. No. 3,702,866 (Argauer et al.), incorporated by reference.

The oligomerization catalysts preferred for use herein include the medium pore shape-selective crystalline aluminosilicate zeolites having a silica-to-alumina ratio of at least 12, a Constraint Index of about 1 to 12 and acid cracking activity of about 10–250. In the fluidized bed reactor the coked catalyst may have an apparent activity (alpha value) of about 10 to 80 under the process conditions to achieve the required degree of reaction severity. Representative of the medium-pore zeolites are ZSM-5, ZSM-11, ZSM-12, ZSM-22, ZSM-23, ZSM-35, and ZSM-48. ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,046,839; 4,375,573; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt. % silica and/or alumina binder.

These siliceous zeolies may be employed in their acid forms ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of Group IB, IIB, IIIB, Va, VIA or VIIIA of the periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g. ionic Ni$^{+2}$, and a shape-selective medium pore acidic oligomerization catalyst, such as ZSM-5 zeolite) which components may be present in admixture or combined in a unitary bifunctional solid particle.

Certain medium pore shape selective catalysts are sometimes known as pentasils. In addition to the preferred aluminosilicates, the borosilicate, ferrosilicate and "silicalite" materials may be employed. It is advantageous to employ a medium-pore zeolite having a silica:alumina molar ratio of 25:1 to 70:1 with an apparatus alpha value of 10–80 to convert 60 to 100 percent, preferably at least 70%, of the olefins in the feedstock.

Medium-pore pentasil zeolites are particularly useful in the process because of their regenerability, long life and stability under the extreme conditions of operation. Usually the zeolite crystals have a crystal size from about 0.01 to cover 2 microns or more, with 0.92–1 micron being preferred. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. In the description of preferred embodiments a 25% H-ZSM-5 catalyst contained within a silica-alumina matrix and having a fresh alpha value of about 80 is employed unless otherwise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds. Maintenance of a turbulent regime is of particular importance in the regenerator under the mild regeneration conditions of the present invention.

DESCRIPTION OF THE PREFERRED EMBODIMENT

Referring now to FIG. 1, feed gas rich in $C_2$–$C_3$ olefins passes under pressure through conduit 10, with the main flow being directed through the bottom inlet of reactor vessel 20 for distribution through grid plate 22 into the fluidization zone 24. Here the feed gas contacts the turbulent bed of finely divided catalyst particles. Reactor vessel 20 is shown provided with heat exchange tubes 26, which may be arranged as several separate heat exchange tube bundles so that temperature control can be separately exercised over different portions of the fluid catalyst bed. The bottom of the tubes are spaced above feed distributor grid 22 sufficiently to be free of jet action by the charged feed through the small diameter holes in the grid. Alternatively, reaction heat can be partially or completely removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction can be controlled by adjusting feed temperature in a known manner.

Catalyst outlet means 28 is provided for withdrawing catalyst from above bed 24 and passed for catalyst regeneration in vessel 30 via control valve 29. The partially deactivated catalyst is oxidatively regenerated by controlled contact with air or other regeneration gas at moderate temperature in a turbulent fluidized-bed regeneration zone to remove carbonaceous deposits and restore acid acitivity. The catalyst particles are entrained in a lift gas and transported via riser tube 32 to a top portion of vessel 30. Air is distributed at the bottom of the bed to effect fluidization, with oxidation by-products being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40, and compressor 42 for return to the vessel with fresh oxidation gas via line 44 and as lift gas for the catalyst in riser 32.

Under optimized process conditions the turbulent fluidized-bed regeneration zone has a superficial vapor velocity of about 0.3 to 2 meters per second (m/sec). At higher velocities entrainment of fine particles may become excessive and beyond about 3 m/sec the entire bed may be transported out of the regeneration zone. At lower velocities, the formation of large bubbles or gas voids can be detrimental to combustion of coke deposits. Even fine particles cannot be maintained effectively in a turbulent bed below about 0.1 m/sec.

A convenient measure of turbulent fluidization is the bed density. A typical turbulent bed has an operating density of about 100 to 500 kg/m$^3$, preferrably about 300 to 500 kg/m$^3$, measured at the bottom of the regeneration zone, becoming less dense toward the top of the regeneration zone, due to pressure drop and particle size differentiation. This density is generally between the catalyst concentration employed in dense beds and the dispersed transport systems. Pressure differential between two vertically spaced points in the regenerator can be measured to obtain the average bed density at such portion of the regeneration zone. For instance, in a fluidized bed system employing ZSM-5 particles having an apparent packed density of 750 kg/m$^3$ and density of 2430 kg/m$^3$, an average fluidized bed density of about 300 to 500 kg/m$^3$ is satisfactory.

As the superficial gas velocity is increased in the dense bed, large gas bubbles occur and with a further increase in the superficial gas velocity the bubbles break down resulting in a turbulent regime. The transition velocity at which this turbulent regime occurs appears to decrease with particle size. The turbuletn regime extends from the transition velocity to the so-called transport velocity, as described by Avidan et al. in U.S. Pat. No. 4,547,616, incorporated herein by reference. As the transport velocity is approached, there is a sharp increase in the rate of particle carryover, and in the absence of solid recycle, the bed could empty quickly.

Several useful parameters contribute to fluidization in the turbulent regime in accordance with the process of the present invention. When employing a medium-pore zeolite catalyst in fine powder form such a catalyst should comprise the zeolite suitably bound or impregnated on a suitable support with a solid density (weight of a representative individaul particle divided by its apparent "outside" volume) in the range from 0.6–2 g/cc, preferably 0.9–1.6 g/cc. The catalyst particles can be in a wide range of particle sizes up to about 250 microns, with an average particle size between about 20 and 100 microns, preferably in the range of 10–150 microns and with the average particle size between 40 and 80 microns. When these solid particles are placed in a fluidized bed where the superficial fluid velocity is 0.3–2, operation in the turbulent regime is obtained. The velocity specified here is for an operation at a total reactor pressure of about 100 to 300 kPa. Those skilled in the art will appreciate that at higher pressures, a lower gas velocity may be employed to ensure operation in the turbulent fluidization regime.

Regenerated catalyst is passed to the main reactor 20 through conduit 46 provided with flow control valve 48. The regenerated catalyst may be lifted to the catalyst bed with pressurized feed gas through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separatos 52, 54 are provided with diplegs 52A, 54A to return any entrained catalyst fines to the lower bed. These separators are positioned in an upper portion of the reactor vessel comprising dispersed catalyst phase 24. Filters, such as sintered metal plate filters, can be used alone or conjunction with cyclones.

The product effluent separated from catalyst particles in the cyclone separating system is then withdrawn from the reactor vessel 20 through top gas outlet means 56. The recovered hydrocarbon product comprising $C_5+$ olefins and/or aromatics, paraffins and naphthenes is thereafter processed as required to provide a desired gasoline or higher boiling product.

The reactor can assume any technically feasible configuration, but several important criteria should be considered. The bed of catalyst in the reactor can be at least about 5–20 meters in height, preferably about 9 meters. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

This process can be used with any process stream which contains sufficient light olefins and paraffins. For example, it can be used to process FCC by-product fuel gas, which typically contains about 10 to 40 wt. % total ethene and propene. Experimental runs are performed using a ZSM-5 catalyst to demonstrate the inventive process. The fluidized bed unit can be operated over a wide range of process variables and catalyst activity.

EXAMPLES

Examples 1 and 2 show relative catalyst makeup rates for an olefin isomerization processing using a conventional high temperature regeneration and the low temperature regeneration process of the present invention. As indicated in Table 1, the low temperature catalyst regeneration is equally effective to maintain gasoline product quality while reducing catalyst makeup requirements by more than 90% by weight.

Figure 2:
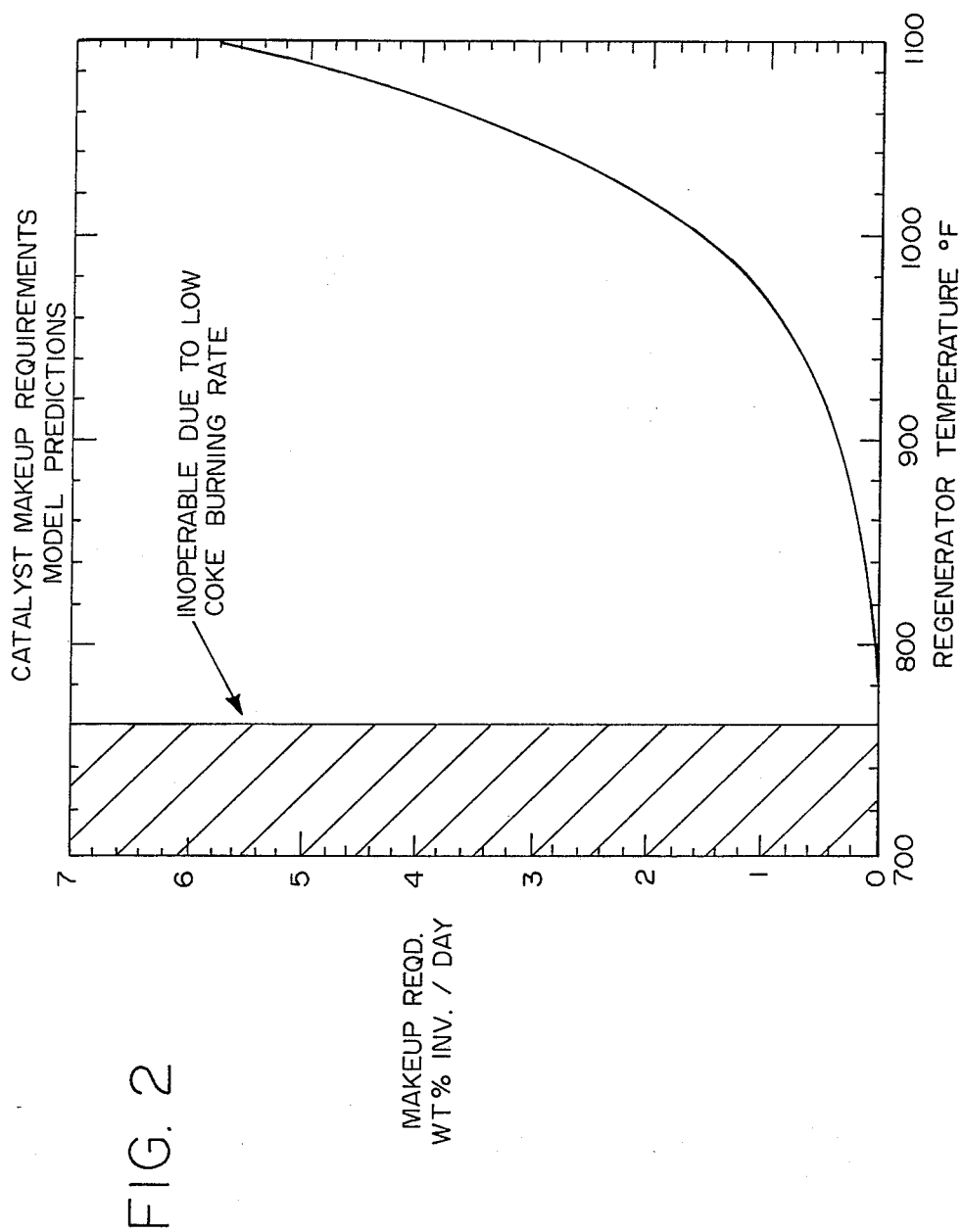
FIG. 2 is a graph summarizing the results of a computer model of catalyst makeup requirement as a function of regenerator temperature.

FIG. 2 illustrates predicted catalyst makeup as a function of regenerator temperature.

TABLE 1

|  | Example 1 (Comparative) | Example 2 |
|---|---|---|
| Operating Conditions |  |  |
| Catalyst activity, | 3 | 3 |
| Regeneration Temp., °C. (°F.) | 502(935) | 427(800) |
| Carbon on Spent Catalyst, wt. % | 1.06 | 1.25 |
| Carbon on Regen. Catalyst, wt. % | 0.05 | 0.27 |
| Reactor Cat. Turnover Time, $hr^{-1}$ | 7 | 7 |
| Reactor Temperature, °C. (°F.) | 427(800) | 427(800) |
| Olefin WHSV, $hr^{-1}$ | 0.37 | 0.37 |
| Yields |  |  |
| $C_5+$ Gasoline, wt. % | 59.9 | 59.9 |
| $C_4+$ Gasoline, wt. % | 83.7 | 84.0 |
| $C_5+$ Gasoline Properties |  |  |
| RON + O | 96.1 | 96.3 |
| MON + O | 83.4 | 83.6 |
| Sg | 0.747 | 0.749 |
| RVP | 7.4 | 7.4 |
| Mol Wt. | 94.0 | 94.1 |
| Catalyst Makeup, Wt. % Inventory/days |  |  |
| Demonstrated | 0.6 | 0.05 |
| Model Prediction | 0.6 | 0.03 |

We claim:

1. A fluidized bed catalytic process for conversion of light olefinic gas feedstock comprising at least 2 mol % ethene and a total $C_2$–$C_3$ alkene content about 10 to 75 wt %, comprising the steps of
   (a) maintaining a fluidized bed of zeolite catalyst particles in a turbulent reactor bed at a temperature of about 315° to 510° C., said catalyst having an apparent particle density of about 0.9 to 1.6 g/cm$^3$ and a size range of about 1 to 150 microns, and average catalyst particle size of about 20 to 100 microns containing about 10 to 25 wt. % of fine particles having a particle size less than 32 microns;
   (b) passing hot feedstock vapor upwardly through the fluidized catalyst bed in a single pass under turbulent flow conditions at reaction severity conditions sufficient to convert at least about 70% of feedstock ethene whereby said catalyst is deactivated;
   (c) maintaining turbulent fluidized bed conditions through the reactor bed between transition velocity and transport velocity at a superficial fluid velocity of about 0.3 to 2 meters per second;
   (d) recovering hydrocarbon product containing a major amount of $C_4+$ hydrocarbons and containing propane and propene in the ratio of about 0.2:1 to 5:1 in the substantial absence of added feedstock propane;
   (e) withdrawing at least a portion of said deactivated catalyst from said reactor bed;
   (f) maintaining a fluidized bed of deactivated catalyst in a turbulent regenerator bed at a temperature between 400° to 482° C.;
   (g) passing oxygen-containing gas upwardly through the fluidized bed or deactivated catalyst at a rate sufficient to maintain the catalyst in a state of turbulent fluidization whereby the deactivated catalyst is regenerated;
   (h) withdrawing regenerated catalyst from the regenerator bed; and
   (i) returning the regenerated catalyst to the reactor bed.

2. The process of claim 1 further comprising returning the regenerated catalyst to the reactor bed at a rate to control catalyst activity such that the $C_2$–$C_5$ alkane:alkene weight ratio in the hydrocarbon product is maintained at about 0.1:1 to 200:1 under conditions of reaction severity to effect feedstock conversion.

3. A fluidized bed process according to claim 1 wherein the reactor bed density is about 100 to 500 kg/m$^3$, measured at the bottom of the bed, wherein the catalyst comprises a siliceous metallosilicate acid zeolite having the structure of ZSM-5 zeolite, and wherein the regenerator bed density is about 100 to 500 kg/m$^3$, measured at the bottom of the bed.

4. The process of claim 1 wherein the feedstock consists essentially of light cracking gas comprising about 2 to 40 wt % ethene in the turbulent reactor bed, which has a bed height of at least 7 meters.

5. The process of claim 1 wherein the superficial feedstock vapor velocity is about 0.3–2 m/sec; the reaction temperature is about 315° to 510° C.; the weight hourly feedstock space velocity (based on olefin equivalent and total reactor catalyst inventory) is about 0.1 to 5; the $C_3$–$C_5$ alkane:alkene weight ratio is about 0.2:1 to 5:1; the average fluidized bed density measured at the reaction zone bottom is about 300 to 500 kg/m$^3$; the regeneration gas superficial vapor velocity is about 0.3–2 m/sec; the regeneration bed temperature is about 400° to 482° C.; and the average fluidized regeneration bed density is about 300 to 500 kg/m$^3$.

6. The process of claim 5 wherein the zeolite catalyst comprises a zeolite having a Constraint Index between about 1 and 12.

7. The process of claim 6 wherein the zeolite catalyst comprises a zeolite having the structure of at least one selected from the group consisting of ZSM-5, ZSM-11, ZSM-22, ZSM-23, ZSM-35, and ZSM-48.

8. The process of claim 7 wherein the zeolite catalyst comprises a zeolite having the structure of ZSM-5.

9. The process of claim 6 wherein the zeolite catalyst has an apparent alpha value of about 1 to 80, and average particle size of about 20 to 100 microns.

10. The process of claim 9 wherein the reactor catalyst bed comprises at least 10 wt. % fine particles having a particle size less than 32 microns.

11. The process of claim 9 wherein the catalyst particles comprise about 5 to 95 wt. % ZSM-5 zeolite having a crystal size of about 0.02–2 microns.

12. The process of claim 4 wherein said feedstock consists essentially of $C_1$–$C_4$ light hydrocarbon cracking gas containing at least 50 wt. % $C_1$–$C_4$ aliphatic hydrocarbons.

13. The process of claim 12 wherein the olefin partial pressure is at least 50 kPa.

14. The process of claim 4 wherein the feed contains a substantial amount of $C_3$–$C_4$ aliphatics, including up to 80 wt. % of propene, with thermodynamic heat balance of paraffinic and olefinic components whereby heat exchange is minimized.

15. The process of claim 3 wherein $C_4-$ hydrocarbon product is separated rom the $C_5+$ product and is recycled back to the reactor at a recycle ratio of 0.1:1 to 5:1 (mol/mol to fresh feed).

16. The process of claim 3 wherein the reactor column contains vertical, horizontal, or a combination of vertical and horizontal heat exchanger tubes to remove reaction heat and control reaction temperature.

17. A process according to claim 3 wherein hydrocarbon gas product is measured to determine propane:propene ratio and reaction severity conditions are adjusted to maintain the propane:propene weight ratio from about 0.2:1 to 50:1.

* * * * *

UNITED STATES PATENT AND TRADEMARK OFFICE
CERTIFICATE OF CORRECTION

PATENT NO. : 4,873,389
DATED : October 10, 1989
INVENTOR(S) : A. Avidan et al.

It is certified that error appears in the above-identified patent and that said Letters Patent is hereby corrected as shown below:

| | |
|---|---|
| Col. 1, line 49 | "temperatrue" should be --temperature-- |
| Col. 2, line 11 | "incorpoated" should be --incorporated-- |
| Col. 2, line 30 | "vessle" should be --vessel-- |
| Col. 4, line 51 | "exchaning" should be --exchanging-- |
| Col. 6, line 46 | "Va" should be --VA-- |
| Col. 6, line 46 | "periodic" should be --Periodic-- |
| Col. 7, line 5 | "cover" should be --over-- |
| Col. 7, line 5 | "0.92" should be --0.02-- |
| Col. 8, line 47 | "turbuletn" should be --turbulent-- |
| Col. 8, line 60 | "individaul" should be --individual-- |
| Col. 9, line 16 | "separatos" should be --separators-- |
| Col. 12, claim 15, line 24 | "rom" should be --from-- |

Signed and Sealed this

Sixth Day of November, 1990

Attest:

HARRY F. MANBECK, JR.

*Attesting Officer*     *Commissioner of Patents and Trademarks*